US010457930B2

(12) United States Patent
Ishizuka et al.

(10) Patent No.: US 10,457,930 B2
(45) Date of Patent: Oct. 29, 2019

(54) OIL-BASED MATERIAL-PRODUCING METHOD AND OIL-BASED MATERIAL-PRODUCING APPARATUS

(75) Inventors: Akinori Ishizuka, Ibaraki (JP); Iwao Yoshino, Ibaraki (JP); Yasunori Tsukahara, Suita (JP)

(73) Assignees: MICROWAVE CHEMICAL CO., LTD., Ibaraki, Osaka (JP); OSAKA UNIVERSITY, Suita, Osaka (JP)

( * ) Notice: Subject to any disclaimer, the term of this patent is extended or adjusted under 35 U.S.C. 154(b) by 0 days.

(21) Appl. No.: 13/807,865

(22) PCT Filed: Jun. 30, 2011

(86) PCT No.: PCT/JP2011/065019
§ 371 (c)(1),
(2), (4) Date: Dec. 31, 2012

(87) PCT Pub. No.: WO2012/002483
PCT Pub. Date: Jan. 5, 2012

(65) Prior Publication Data
US 2013/0102047 A1    Apr. 25, 2013

(30) Foreign Application Priority Data
Jun. 30, 2010   (JP) ................. 2010-150047

(51) Int. Cl.
C12N 13/00     (2006.01)
C12M 1/00      (2006.01)
C12N 1/12      (2006.01)
C12P 7/64      (2006.01)

(52) U.S. Cl.
CPC ............. C12N 13/00 (2013.01); C12M 47/06 (2013.01); C12N 1/12 (2013.01); C12P 7/6463 (2013.01)

(58) Field of Classification Search
CPC ....... C12M 47/06; C12P 7/6463; C12N 13/00
USPC .......................................... 435/173.7, 283.1
See application file for complete search history.

(56) References Cited

U.S. PATENT DOCUMENTS

| 3,463,627 | A | | 8/1969 | Le Blanc |
| 4,269,805 | A | | 5/1981 | Schoengen et al. |
| 4,279,722 | A | * | 7/1981 | Kirkbride ................ 204/157.15 |
| 4,718,358 | A | | 1/1988 | Nomi et al. |
| 4,844,838 | A | | 7/1989 | Ohtsuka et al. |
| 5,393,320 | A | | 2/1995 | Gomez |
| 5,458,897 | A | * | 10/1995 | Pare ............................. 426/241 |
| 5,822,879 | A | | 10/1998 | Vincent et al. |
| 6,484,539 | B1 | | 11/2002 | Nordine et al. |
| 6,723,999 | B2 | * | 4/2004 | Holl ............................. 250/438 |
| 7,087,220 | B2 | | 8/2006 | Li |
| 7,348,182 | B2 | * | 3/2008 | Martin et al. ................ 436/518 |
| 8,328,997 | B2 | | 12/2012 | Charlier de Chily et al. |

| 2004/0056026 | A1 | 3/2004 | Jakes et al. |
| 2006/0228088 | A1 | 10/2006 | Charlier de Chily et al. |
| 2006/0237300 | A1 | 10/2006 | Stroder et al. |
| 2007/0295717 | A1 | 12/2007 | Horikawa et al. |
| 2010/0017220 | A1 | 1/2010 | Lowenstein |
| 2010/0025227 | A1 | 2/2010 | Charlier de Chily et al. |
| 2011/0263843 | A1 | 10/2011 | Watanabe et al. |
| 2013/0102804 | A1 | 4/2013 | Charlier de Chily et al. |

FOREIGN PATENT DOCUMENTS

| CN | 1729049 | 2/2006 |
| CN | 101954266 A | 1/2011 |
| EP | 0626871 B1 | 4/1997 |
| EP | 2727647 A1 | 5/2014 |
| JP | S 51-041679 | 4/1976 |
| JP | S 52-35350 | 3/1977 |
| JP | S 59-004431 | 1/1984 |
| JP | S 63-198899 | 8/1988 |
| JP | S 63-285121 | 11/1988 |
| JP | H 0266497 | 3/1990 |
| JP | H 03-109296 U | 11/1991 |
| JP | H06-041545 | 2/1994 |
| JP | H 07-258117 | 10/1995 |
| JP | H07309433 A | 11/1995 |
| JP | H 08-501016 | 2/1996 |
| JP | H08242783 A | 9/1996 |
| JP | H09285282 A | 11/1997 |
| JP | H 1050470 | 2/1998 |
| JP | 2001009009 A | 1/2001 |
| JP | 2002-079078 | 3/2002 |
| JP | 2004-201967 | 7/2004 |
| JP | 2004-216200 | 8/2004 |
| JP | 2006-511775 | 4/2006 |
| JP | 20060512554 | 4/2006 |
| JP | 2006-516008 | 6/2006 |
| JP | 2006-257304 | 9/2006 |
| JP | 2007-000774 | 1/2007 |

(Continued)

OTHER PUBLICATIONS

Itaya et al., 2005, Drying Technology, 23, 273-287.*
Crespo M.O. Punin, et al., "Extraction of Hydrocarbons from Seaweed Samples Using Sonication and Microwave-Assisted Extraction: A Comparative Study", J. Chromatogr. Sci., 2006, vol. 44, No. 10, p. 615-618.
Hattab M.E., et al., "Comparison of various extraction methods for identification and determination of volatile metabolites from the brown alga *Dictyopteris membranacea*", J. Chromatogr. A, 2007, vol. 1143, p. 1-7.
Hattab M.E., et al., "Isolation of the Volatile Compounds from the Brown Alga *Dictyopteris membranacea* by Focused Microwave-Assisted Hydrodistillation", J. Essent. Oil Res., 2002, vol. 14, No. 6, p. 422-424.

(Continued)

*Primary Examiner* — Nghi V Nguyen
(74) *Attorney, Agent, or Firm* — Troutman Sanders LLP

(57) ABSTRACT

An oil-based material-producing method includes a microwave irradiation step of irradiating oil-based material-producing microorganisms with microwaves. The oil-based material-producing method may also include a collecting step of collecting an oil-based material produced by the oil-based material-producing microorganisms after the microwave irradiation step.

18 Claims, 6 Drawing Sheets

(56) References Cited

FOREIGN PATENT DOCUMENTS

| | | | | |
|---|---|---|---|---|
| JP | 2007-059317 | 3/2007 | | |
| JP | 2007-059318 | 3/2007 | | |
| JP | 2007-222696 | 9/2007 | | |
| JP | 2007-307440 | 11/2007 | | |
| JP | 2007-326013 | 12/2007 | | |
| JP | 2008-302281 | 12/2008 | | |
| JP | 2009-183198 A | 8/2009 | | |
| JP | 2010-111865 A | 5/2010 | | |
| JP | 2010-184230 | 8/2010 | | |
| JP | 2011-235262 | 11/2011 | | |
| JP | 2011-235263 | 11/2011 | | |
| WO | WO 1993/014821 | 8/1993 | | |
| WO | 2004056468 A1 | 7/2004 | | |
| WO | WO 2004/056471 | 7/2004 | | |
| WO | WO 2004/066683 | 8/2004 | | |
| WO | WO 2005/102510 | 11/2005 | | |
| WO | 2006/109588 A1 | 10/2006 | | |
| WO | WO-2008073186 A2 * | 6/2008 | ............... | C08H 8/00 |
| WO | 20091110245 A1 | 9/2009 | | |
| WO | 2009/149027 A2 | 12/2009 | | |
| WO | WO 2010/013696 | 2/2010 | | |

OTHER PUBLICATIONS

Uy F. Sandra, et al. "Seaweed processing using industrial single-mode cavity microwave heating: a preliminary investigation", Carbohydr. Res., 2005, vol. 340, No. 7, p. 1357-1364.
International Search Report dated Aug. 23, 2011, which issued during the prosecution of International Application No. PCT/JP2011/064965.
International Search Report dated Jan. 29, 2013, from corresponding International Application No. PCTJP2012/079152.
Ishizuka, A. et al. "Microwave Chemical Process: Process Innovation and Application" Fine Chemical, 2011, vol. 40, No. 3, pp. 42-46.
Japanese Office Action, dated Aug. 3, 2011, which issued during the prosecution of Japanese Patent Application No. 2010-111270.
Japanese Office Action, dated Oct. 31, 2013, which issued during the prosecution of Japanese Patent Application No. 2010-111271.
Japanese Search Report dated Jun. 2, 2010, prepared for Japanese Patent Application No. 2010-111271.
Japanese Search Report dated May 31, 2010, prepared for Japanese Patent Application No. 2010-111270.
Written Opinion dated Aug. 23, 2011, which issued during the prosecution of International Application No. PCT/JP2011/064965.
Chinese Office Action dated Oct. 30, 2014, which issued during prosecution of Chinese Application No. 201180071600.1.
Supplementary European Search Report dated Feb. 26, 2015 which issued during prosecution of EP Application No. 11868832.4.
Chinese Office Action dated Feb. 2, 2015 which issued during prosecution of CN Application No. 201280062762.3.
Office Action dated Apr. 1, 2015 which issued during prosecution of U.S. Appl. No. 14/357,145.
Office Action dated Apr. 1, 2015 which issued during prosecution of U.S. Appl. No. 14/357,172.
Japanese Office Action dated May 29, 2015, which issued during prosecution of Japanese Application No. 2012-522686.
Chinese Office Action dated Jun. 25, 2015, which issued during prosecution of Chinese Application No. 201180071600.1.
Office Action dated Jul. 9, 2015 which issued during prosecution of U.S. Appl. No. 13/807,865.
Extended European Search Report dated Jul. 13, 2015 which issued during prosecution of EP Application No. 12848355.9.
Extended European Search Report dated Jul. 20, 2015 which issued during prosecution of EP Application No. 12848048.0.
Office Action dated Aug. 18, 2015 which issued during prosecution of U.S. Appl. No. 14/357,145.
Office Action dated Aug. 19, 2015 which issued during prosecution of U.S. Appl. No. 14/357,172.
Chinese Office Action dated Sep. 22, 2015 during the prosecution of Chinese Patent Application No. 201280062750.0.
Chinese Office Action dated Sep. 22, 2015 during the prosecution of Chinese Patent Application No. 201280062762.3.
Japanese Office Action dated Nov. 25, 2015 during the prosecution of Japanese Patent Application No. 2012-522686.
Notification of Result of Substantive Examination issued for Indonesian Patent Application No. P-00201400520 dated Jan. 18, 2019.
Final Office Action issued for U.S. Appl. No. 15/398,877 dated Feb. 11, 2019.
Communication issued for European Patent Application No. 11868832.4 dated Feb. 26, 2019.
Office Action issued in U.S. Appl. No. 14/123,174 dated Jul. 19, 2018.
Search report issued in Brazilian Application BR112013033215-8 dated May 18, 2018. With English Translation.
First Examination Report for Indian Application No. 534/CHENP/2014 dated Nov. 15, 2018.
Communication pursuant to Article 94(3) EPC for European Patent Application No. 12848355.9 dated Dec. 12, 2018.
Office Action for U.S. Appl. No. 14/123,174 dated Jan. 14, 2019.
U.S. Office Action dated Aug. 18, 2018 for U.S. Appl. No. 15/398,877.
Technical Examination Report dated Oct. 9, 2018 for Brazilian Application No. 112013033215.
Communication pursuant to Article 94(3) EPC issued in corresponding European Patent Application No. 12 848 048.0 dated Jul. 22, 2019.
Office Action issued in U.S Appl. No. 14/123,174 dated Jun. 24, 2019.

* cited by examiner

Reactor 11

OIL-BASED MATERIAL-PRODUCING METHOD AND OIL-BASED MATERIAL-PRODUCING APPARATUS

CROSS-REFERENCE TO RELATED APPLICATIONS

The present application is a 371 of International Application No. PCT/JP2011/065019, filed Jun. 30, 2011, which claims priority to Japanese Patent Application No. 2010-150047 filed Jun. 30, 2010. The entire contents of each of the above-noted related applications are hereby incorporated herein by reference.

TECHNICAL FIELD

The present invention relates to a method and an apparatus for producing an oil-based material using oil-based material-producing microorganisms.

BACKGROUND ART

Conventionally, there is a proposed method for producing an oil-based material such as a hydrocarbon using microalgae, as described in, for example, Japanese Patent Application Publication No. H6-41545A.

SUMMARY OF INVENTION

In the production of an oil-based material using oil-based material-producing microorganisms such as microalgae, there has been a demand for the development of a simpler method for producing such a material using the oil-based material-producing microorganisms.

The present invention was arrived at in view of these circumstances, and it is an aspect of the present invention to provide a method for producing an oil-based material, with which such a material can be produced using oil-based material-producing microorganisms with a simple method.

In order to achieve the above-described aspect, the present invention is directed to an oil-based material-producing method, including a microwave irradiation step of irradiating oil-based material-producing microorganisms with microwaves (e.g., electromagnetic waves).

With this configuration, if microwaves are irradiated, for example, at least part of the cell walls of the oil-based material-producing microorganisms can be broken. As a result, the oil-based material that is present inside the oil-based material-producing microorganisms can be collected.

Furthermore, in the above-described oil-based material-producing method according to the, in the microwave irradiation step, microwaves may be irradiated in the presence of a microwave responsive material, which is either one of a microwave-absorbing material and a microwave-sensitive material.

With this configuration, the electric field and the magnetic field of microwaves are concentrated on the microwave responsive material. As a result, for example, at least part of the cell walls of the oil-based material-producing microorganisms that are present near the microwave responsive material can be broken.

Furthermore, in the above-described oil-based material-producing method, the microwave responsive material may be able to flow.

With this configuration, if the microwave responsive material flows near the oil-based material-producing microorganisms, for example, at least part of the cell walls of the oil-based material-producing microorganisms can be broken.

Furthermore, in the above-described oil-based material-producing method, the microwave responsive material may have a shape for collecting electric field of microwaves.

With this configuration, the electric field of microwaves is concentrated on the microwave responsive material, and, for example, at least part of the cell walls of the oil-based material-producing microorganisms that are present near the microwave responsive material can be broken.

Furthermore, in the above-described oil-based material-producing method, the microwave responsive material may be immobilized.

With this configuration, for example, at least part of the cell walls of the oil-based material-producing microorganisms that flow near the immobilized microwave responsive material can be broken.

Furthermore, in the above-described oil-based material-producing method, the microwave responsive material may be at least any one of a dielectric, a conductive substance, and a magnetic substance.

Furthermore, the above-described oil-based material-producing method may further include a collecting step of collecting an oil-based material produced by the oil-based material-producing microorganisms after the microwave irradiation step.

With this configuration, the collecting step makes it possible, for example, to collect the oil-based material that is present inside the oil-based material-producing microorganisms.

Furthermore, in the above-described oil-based material-producing method, the oil-based material-producing microorganisms may be oil-based material-producing microalgae.

Moreover, another aspect of the present invention provides an apparatus to produce an oil-based material, with which such a material can be produced using oil-based material-producing microorganisms.

In order to achieve the above-described another aspect, the present invention is directed to an oil-based material-producing apparatus including a reactor, in which oil-based material-producing microorganisms are placed, and a microwave generator that irradiates the oil-based material-producing microorganisms in the reactor with microwaves.

With this configuration, if microwaves are irradiated, for example, at least part of the cell walls of the oil-based material-producing microorganisms can be broken. As a result, the oil-based material that is present inside the oil-based material-producing microorganisms can be collected.

Furthermore, in the above-described oil-based material-producing apparatus, a microwave responsive material, which is either one of a microwave-absorbing material and a microwave-sensitive material, may be present in the reactor.

With this configuration, the electric field and the magnetic field of microwaves are concentrated on the microwave responsive material. As a result, for example, at least part of the cell walls of the oil-based material-producing microorganisms that are present near the microwave responsive material can be broken.

Furthermore, in the above-described oil-based material-producing apparatus, at least part of the reactor may have a shape that allows microwaves generated by the microwave generator to be concentrated and irradiated thereon.

With this configuration, the oil-based material-producing microorganisms are effectively irradiated with microwaves at the position of the reactor on which microwaves are concentrated and irradiated, and, for example, at least part of the cell walls of the oil-based material-producing microorganisms can be more effectively broken.

The above-described method and apparatus for producing an oil-based material make it possible to collect the material produced by oil-based material-producing microorganisms, by irradiating the oil-based material-producing microorganisms with microwaves. Thus, the oil-based material can be produced using the oil-based material-producing microorganisms with a simple method.

DETAILED DESCRIPTION

Figure 1:
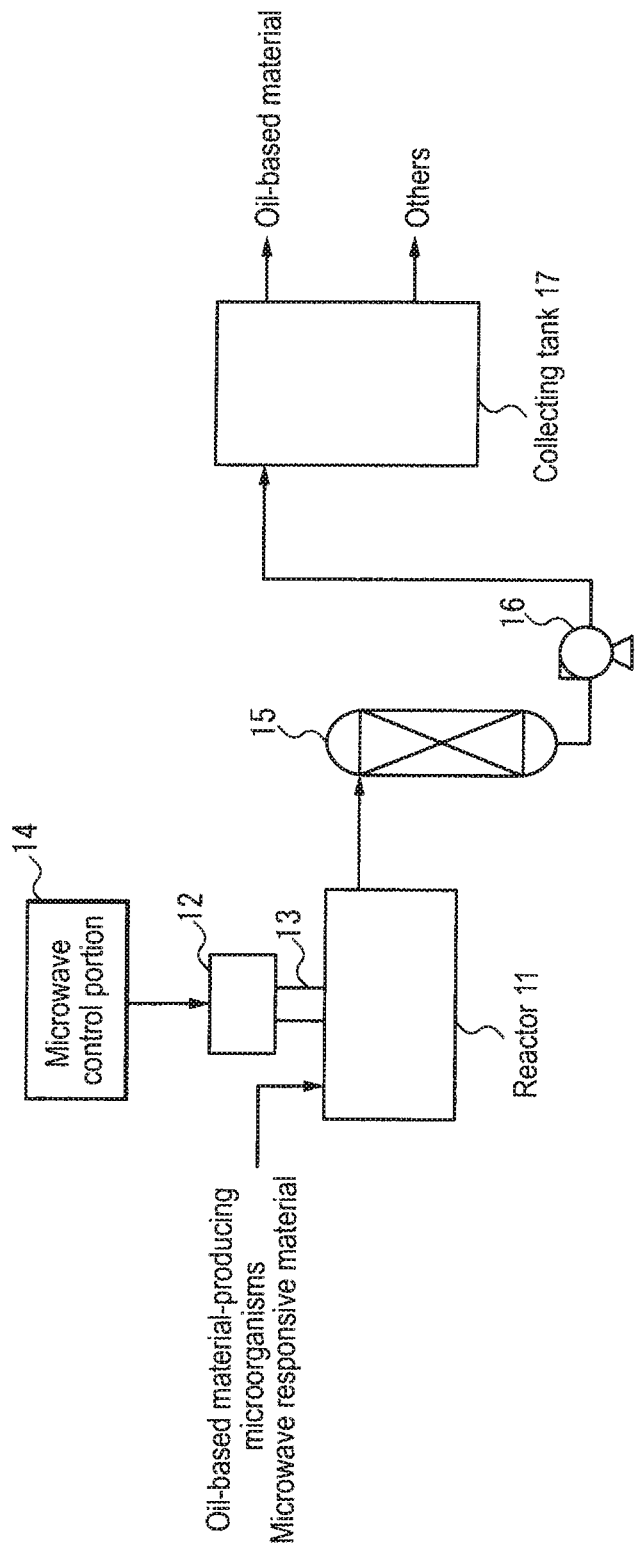
FIG. 1 is a diagram showing the configuration of an oil-based material-producing apparatus according to an example of the present invention.

Hereinafter, an oil-based material-producing method according to the aspect of the present invention will be described by way of an example. Note that constituent elements and steps denoted by the same reference numerals are the same as or correspond to each other in the following example, and, thus, a description thereof may not be repeated.

Below, an oil-based material-producing apparatus according to the another aspect of the present invention will be described with reference to the drawings. The oil-based material-producing apparatus according to an example in the another aspect irradiates oil-based material-producing microorganisms with microwaves.

FIG. 1 is a diagram showing the configuration of an oil-based material-producing apparatus 1 according to this example. The oil-based material-producing apparatus 1 according to this example includes a reactor 11, a microwave generator 12, a waveguide 13, a microwave control portion 14, a microwave responsive material separating portion 15, and a collecting tank 17.

In the reactor 11, oil-based material-producing microorganisms and a microwave responsive material are placed. There is no limitation on the type of oil-based material-producing microorganisms, as long as they are microorganisms that produce an oil-based material when cultured. The oil-based material-producing microorganisms may produce an oil-based material, for example, through photosynthesis. The oil-based material-producing microorganisms produce an oil-based material, and store the produced oil-based material inside their cells. The oil-based material-producing microorganisms may store the produced oil-based material outside their cells as well. Examples of the oil-based material include a hydrocarbon and a lipid. Examples of the lipid include a neutral lipid and a fatty acid. The oil-based material is used as a fuel without any treatment or after predetermined treatment. The fuel is used, for example, in an internal combustion engine of automobiles or the like. Note that other materials may be placed in the reactor 11 together with the oil-based material-producing microorganisms and the microwave responsive material. For example, water may be placed in the reactor 11 together with the oil-based material-producing microorganisms and the microwave responsive material. The water may be pure water or may be ultrapure water.

Examples of the oil-based material-producing microorganisms include oil-based material-producing microalgae. There is no particular limitation on the oil-based material-producing microalgae, as long as they are microalgae that produce an oil-based material. Examples of the oil-based material-producing microalgae include *Botryococcus braunii*, *Pseudochoricystis ellipsoidea*, *Scenedesmus* (e.g., *Scenedesmus rubescens*), which is a green alga, *Euglena*, and *Navicula* (e.g., *Navicula* sp.), which is a diatom. *Botryococcus braunii* produces, for example, linear alkadienes or alkatrienes having carbon atoms in an odd number of 25 to 31, or polymethylated triterpenes ($C_nH_{2n-10}$) having 30 to 37 carbon atoms. *Pseudochoricystis ellipsoidea* produces, for example, saturated or unsaturated aliphatic hydrocarbons having 10 to 25 carbon atoms. Furthermore, *Scenedesmus* produces glycerine ester and the like. Regarding these microalgae, see Patent Document 1 described above, JP 2010-111865A, and WO 2006/109588, for example.

The oil-based material-producing microorganisms that are placed in the reactor 11 may be or may not be in a water-containing state. Examples of the oil-based material-producing microorganisms in a water-containing state include concentrates (e.g., aqueous slurry) obtained by reducing a water content of the cultured oil-based material-producing microorganisms by removing part of the water through dewatering such as filtering. Meanwhile, examples of the oil-based material-producing microorganisms not in a water-containing state include materials obtained by drying or freeze-drying the cultured oil-based material-producing microorganisms. In this example, a case will be described in which the oil-based material-producing microorganisms in a water-containing state are irradiated with microwaves.

Furthermore, the microwave responsive material is either one of a microwave-absorbing material and a microwave-sensitive material. The microwave responsive material flows inside the reactor 11. Accordingly, inside the reactor 11, microwaves are irradiated in the presence of the microwave responsive material. Note that the microwave absorptivity and the microwave sensitivity depend on the frequency of microwaves used for irradiation, the temperature inside the reactor 11, and the like. That is to say, for example, the frequency of microwaves used and the temperature inside the reactor 11 that increase the dielectric loss factor provide a higher microwave absorptivity. Accordingly, for example, such a material having a high microwave absorptivity may be used as the microwave responsive material. Examples of the microwave responsive material include a dielectric, a conductive substance, and a magnetic substance. Examples of the microwave responsive material further include organic materials, carbon except for fullerene (e.g., graphite, carbon nanotube, activated carbon, etc.), metals (e.g., iron, nickel, cobalt, etc.), metal oxide (e.g., ferrite, etc.), and composites of any two or more thereof. Furthermore, the microwave responsive material may be in a shape for collecting the electric field of microwaves. Examples of the shape for collecting the electric field of microwaves include a grain shape having a surface provided with multiple pointed projections (e.g., spheres having a surface provided with multiple outward spikes, etc.) and a shape having a rough surface. If the microwave responsive material is in a grain shape having a surface provided with multiple pointed projections, for example, the electric field of microwaves is concentrated on those pointed projections as in the case of lightning conductors. If the reactor 11 contains the flowing microwave responsive material together with the oil-based material-producing microorganisms, for example, the electric field is concentrated on the microwave responsive material that is present between the oil-based material-producing microorganisms, and, thus, the intensity of the microwaves becomes higher near the microwave responsive material. Accordingly, the oil-based material-producing microorganisms are effectively irradiated with microwaves near the microwave responsive material. As a result, at least part of the cell walls of the oil-based material-producing microorganisms is easily broken, and, thus, the oil-based material inside the cells of the oil-based material-producing microorganisms can be collected. Note that the microwave responsive material may be present in the reactor 11, for example, in a very highly dispersed state.

Furthermore, for example, the reactor 11 may be of a batch type or may be of a flow-through type (flow type). In the former case, a prescribed amount of oil-based material-producing microorganisms and the like are loaded into the reactor 11 and irradiated with microwaves, after which the oil-based material-producing microorganisms and the like in the reactor 11 are simultaneously passed to the subsequent process. On the other hand, in the latter case, the loading of the oil-based material-producing microorganisms and the like into the reactor 11, the microwave irradiation, and the discharge of the oil-based material-producing microorganisms and the like from the reactor 11 are continuously and gradually performed. Furthermore, if the reactor 11 is of a flow-through type, it may be of a horizontal flow-through type or may be of a vertical flow-through type. This example will be described mainly regarding a case in which the reactor 11 is of a horizontal flow-through type. If the reactor 11 is of a horizontal flow-through type, for example, a large amount of material can be treated (e.g., 10 tons or more/day). Preferably, the inner wall of the reactor 11 is made of a material that reflects microwaves. Examples of the material that reflects microwaves include metals. The configuration of the internal portion of the reactor 11 will be described later.

The microwave generator 12 generates microwaves, and irradiates the oil-based material-producing microorganisms in the reactor 11 with the microwaves. The oil-based material-producing apparatus 1 according to this example may be provided with one microwave generator 12, or may be provided with two or more microwave generators 12. There is no limitation on the frequency of the microwaves, and examples thereof include 2.45 GHz, 5.8 GHz, 24 GHz, 913 MHz, and other frequencies ranging from 300 MHz to 300 GHz.

The waveguide 13 transmits the microwaves generated by the microwave generator 12 to the reactor 11. Typically, the number of waveguides 13 provided is the same as the number of microwave generators 12 as shown in FIG. 1. Meanwhile, a branched waveguide 13 may be used to transmit the microwaves generated by the microwave generator 12 to multiple locations of the reactor 11. Preferably, the standard of the waveguide 13 is in accordance with the frequency of microwaves generated by the microwave generator 12.

The microwave control portion 14 controls the power of microwaves with which the reactor 11 is to be irradiated, according to the temperature measured by a temperature measuring portion 24 (described later). The control by the microwave control portion 14 makes it possible to keep the internal portion of the reactor 11 at a desired temperature or in a desired temperature range.

The microwave responsive material separating portion 15 separates the microwave responsive material from the mixture of the oil-based material-producing microorganisms irradiated with microwaves in the reactor 11 and the microwave responsive material. The microwave responsive material separating portion 15 may separate the microwave responsive material, for example, using differences in the size between the oil-based material-producing microorganisms and the microwave responsive material. In this case, for example, a filter may be used to separate the microwave responsive material. Furthermore, the microwave responsive material separating portion 15 may separate the microwave responsive material, for example, using differences in the specific gravity between the oil-based material-producing microorganisms and the microwave responsive material. In this case, for example, one of the oil-based material-producing microorganisms and the microwave responsive material may be deposited to separate the microwave responsive material. Furthermore, if the microwave responsive material contains a magnetic substance, a magnet (e.g., a permanent magnet or an electromagnet) for attracting the microwave responsive material may be used to separate the microwave responsive material. Note that the separated microwave responsive material may be used again as appropriate.

In the collecting tank 17, the material obtained by performing the microwave irradiation and then separating the microwave responsive material in the microwave responsive material separating portion 15 is placed. Then, in the collecting tank 17, the oil-based material produced by the oil-based material-producing microorganisms is collected. This collecting can be performed, for example, with a method as in a separating funnel using differences in the specific gravity between the oil-based material and the other materials. Typically, the oil-based material-producing microorganisms are irradiated with microwaves to be separated into an oil layer, a water layer, and a biomass layer (sediment layer). Since the oil layer has the smallest specific gravity, typically, the uppermost layer in the collecting tank 17 is collected, so that only the oil layer can be collected, that is, the oil-based material produced by the oil-based material-producing microorganisms can be collected. Note that, in order to collect the oil-based material, solvent for dissolving the oil-based material may be used for the collecting. The methods for collecting the oil-based material are already known, and, thus, a detailed description thereof has been omitted.

A cooler (not shown) that cools down the material after the reaction in the reactor 11 may be or may not be provided on the path after the reactor 11. In the former case, for example, the cooler may use water to cool down the material after the reaction in the reactor 11.

Figure 2:
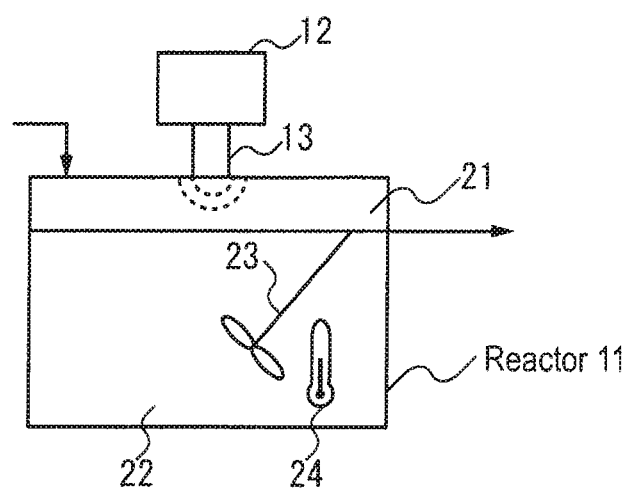
FIG. 2 is a diagram showing an exemplary configuration of the internal portion of a reactor according to the example.

FIG. 2 is a diagram showing an exemplary structure of the internal portion of the reactor 11 according to this example. In FIG. 2, there is an unfilled space 21 in the upper portion inside the reactor 11. The unfilled space 21 is irradiated with microwaves that have been generated by the microwave generator 12 and transmitted via the waveguide 13. Note that, if the reactor 11 is of a vertical flow-through type, typically, there is no unfilled space. Accordingly, in that case, the space filled with the oil-based material-producing microorganisms and the like may be irradiated with microwaves.

Furthermore, as shown in FIG. 2, the reactor 11 also has an agitation unit 23. That is to say, the oil-based material-producing apparatus 1 according to this example may have one or more agitation units 23 that agitate the content inside the reactor 11. In FIG. 2, the agitation unit 23 is in the shape of blades, but this merely schematically shows the agitation unit 23. Examples of the agitation unit 23 include a rotating agitation unit, a bubbling agitation unit, an ultrasonic wave agitation unit, and combinations of any two or more thereof. That is to say, the agitation unit 23 may perform agitation, for example, using any one or more methods of rotating agitation, bubbling agitation, and ultrasonic wave agitation. If the agitation unit 23 performs rotating agitation, the agitation may be performed, for example, by rotating a blade-like member, a wing-like member, a rod-like member, or the like. The rotation may be performed, for example, by rotating a blade-like member or the like attached to a shaft in accordance with the rotation of the shaft, or by using a magnetic force as in the case of a magnetic stirrer. If a magnetic force is used, a magnetic agitator in the shape of a rod, a blade, a wing, or the like is rotated by a magnet. Furthermore, if the reactor 11 is of a flow-through type and performs rotating agitation using a blade-like member or a wing-like member, these may be rotated to cause the content of the reactor 11 to flow in a direction from the upstream to the downstream or in its opposite direction, but there is no limitation to this. Furthermore, if the agitation unit 23 performs bubbling agitation, the agitation may be performed, for example, by blowing a gas into the content inside the reactor 11. Examples of the gas that is to be blown into the content include inert gases such as helium or argon, nitrogen, air, and the like. Furthermore, if the agitation unit 23 performs ultrasonic wave agitation, the agitation may be performed, for example, by generating ultrasonic waves on a bottom face or a side face of the reactor 11 and then irradiating the content of the reactor 11 with the generated ultrasonic waves. Note that rotating agitation, bubbling agitation, and ultrasonic wave agitation are already known, and, thus, a detailed description thereof has been omitted. Furthermore, the agitation unit 23 may perform the agitation using a method other than the above. For example, the agitation unit 23 may perform swinging agitation that swings the reactor 11 itself.

Hereinafter, a reason that the content of the reactor 11 is agitated by the agitation unit 23 will be briefly described. A first reason that the content is agitated by the agitation unit 23 is to uniformly irradiate the content with microwaves. Although depending on the content type, the depth to which microwaves penetrate is fixed, and, thus, the agitation is performed in order to uniformly irradiate the entire content with microwaves. Furthermore, the content can be more efficiently irradiated with microwaves as the surface area of the content at the unfilled space 21 increases. Accordingly, a second reason that the content is agitated is to increase the area subjected to microwave irradiation. Thus, the content is agitated by the agitation unit 23 preferably at an intensity that allows the surface of the content at the unfilled space 21 to be ruffled, but there is no limitation to this (if the agitation is performed for the first reason, it may be sufficient that the entire content is eventually irradiated with microwaves). Since the content is agitated by the agitation unit 23 in this manner, even a content including two or more materials having different densities can be agitated such that they are mixed and reacted as appropriate.

Furthermore, as shown in FIG. 2, the reactor 11 also has the temperature measuring portion 24. That is to say, the oil-based material-producing apparatus 1 according to this example may have the temperature measuring portion 24 that measures the temperature inside the reactor 11. Preferably, the temperature inside the reactor 11 is the temperature of the content of the reactor 11. FIG. 2 schematically shows the temperature measuring portion 24, but the temperature measuring portion 24 may measure the temperature, for example, using a thermocouple, an infrared sensor, an optical fiber, or other methods. The temperature measured by the temperature measuring portion 24 (strictly speaking, data indicating the temperature) is passed to the microwave control portion 14, and is used to control the power of microwaves from the microwave generator 12. This control may be control for keeping the content at a desired temperature or in a desired temperature range as described above.

In the reactor 11 of this example, the height of a liquid surface of a content 22 may be, for example, approximately ½ to ⅚ of the maximum height inside the reactor 11. That is to say, the height of the unfilled space 21 may be, for example, approximately ⅙ to ½ of the maximum height inside the reactor 11. Furthermore, in this example, a case was described in which there is the unfilled space 21 in the reactor 11, there may be no unfilled space 21 in the reactor 11. That is to say, the content 22 may be filled up such that there is no unfilled space 21 in the reactor 11. In that case, since there is no unfilled space that is to be irradiated with microwaves, the space filled with the oil-based material-producing microorganisms and the like is irradiated with microwaves.

Furthermore, there is no limitation on the shape of the reactor 11. Examples of the shape of the reactor 11 include a cylinder that is long in the left-right direction in FIG. 2, a cylinder that is long in the vertical direction, a rectangular solid, and other shapes. In this example, a case will be described in which the reactor 11 is in the shape of a cylinder.

Furthermore, if the reactor 11 is of a flow-through type, the internal portion of the reactor 11 may be partitioned into multiple chambers by partition plates. That is to say, the reactor 11 may have multiple chambers that are continuously arranged in series. In that case, each chamber is preferably irradiated with microwaves. Furthermore, in that case, the content of the reactor 11 passes through each chamber when moving from the upstream to the downstream. Furthermore, each chamber may be or may not be provided with the agitation unit 23. Furthermore, each chamber may be or may not be provided with the temperature measuring portion 24. The partition plates may transmit microwaves or may reflect microwaves. Examples of a material that transmits microwaves include Teflon (registered trademark), quartz glass, ceramic, silicon nitride-alumina, and the like. Accordingly, partition plates that transmit microwaves may be made of such a material that transmits microwaves. Furthermore, examples of a material that reflects microwaves include metals. Accordingly, partition plates that do not transmit microwaves may be made of such a material that reflects microwaves. Furthermore, the wall faces of the reactor 11 may be covered by a heat insulating material. In that case, heat inside the reactor 11 can be prevented from being dissipated to the outside.

Furthermore, it is assumed that, if the reactor 11 has one or more partition plates, a flow path of the content is formed through the partition plates. The flow path allows the content to flow mainly from the upstream side to the downstream side in the reactor 11, but may allow the content to flow partially from the downstream side to the upstream side. The flow path through the partition plates may allow the content, for example, to flow over the upper edges of the partition plates, or to flow through gaps of the partition plates. The gaps of the partition plates may be present, for example, between the partition plates and the inner wall of the reactor 11, or through the partition plates themselves. Preferably, the gaps each have a size that allows at least the content to flow therethrough. Note that there is no limitation on the shape or the number of gaps.

Figure 3:
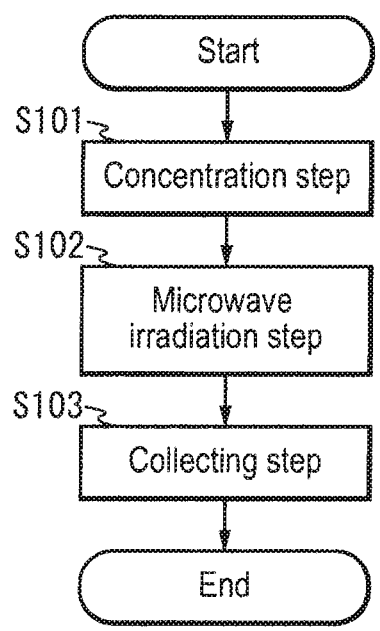
FIG. 3 is a flowchart showing an oil-based material-producing method according to the example.

Next, a method for producing an oil-based material according to the example will be described with reference to the flowchart in FIG. 3.

(Step S101) In a concentration step, oil-based material-producing microorganisms that have been cultured are concentrated. As described above, this concentration can be performed through dewatering such as filtering. Note that, in the oil-based material-producing apparatus 1 in FIG. 1, no constituent element that performs this dewatering is shown. That is to say, it is assumed that an apparatus other than the oil-based material-producing apparatus 1 shown in FIG. 1 performs the dewatering. If the dewatering is not to be performed, step S101 may be omitted.

(Step S102) In a microwave irradiation step, the concentrated oil-based material-producing microorganisms are irradiated with microwaves. Note that this irradiation is performed in the reactor 11. Furthermore, as described above, microwaves may be irradiated in the presence of the microwave responsive material. Furthermore, in the microwave irradiation step, the microwave control portion 14 may perform control such that the temperature of the content of the reactor 11 does not exceed a predetermined temperature. Note that microwaves are irradiated typically at an ordinary pressure. That is to say, microwaves are irradiated at an atmospheric pressure without any application of pressure. In the microwave irradiation step, the oil-based material-producing microorganisms are irradiated with microwaves, for example, to rapidly heat and evaporate moisture in the cells. As a result, at least part of the cell walls of the oil-based material-producing microorganisms can be indirectly broken. Furthermore, with the microwave irradiation, for example, at least part of the cell walls of the oil-based material-producing microorganisms can be directly broken. Furthermore, if the oil-based material-producing microorganisms store the produced oil-based material outside their cells as well, membranes that enclose the oil-based material stored outside the cells can be directly or indirectly broken, for example, by microwave irradiation.

(Step S103) In a collecting step, the oil-based material produced by the oil-based material-producing microorganisms is collected. Specifically, first, the microwave responsive material separating portion 15 separates the microwave responsive material from the mixture of the oil-based material-producing microorganisms irradiated with microwaves and the microwave responsive material. The oil-based material-producing microorganisms from which the microwave responsive material has been separated is placed by a pump 16 into the collecting tank 17, and, in the collecting tank 17, the oil-based material is collected. The oil-based material may be collected, for example, by extracting an oil layer from the material after the microwave irradiation. At that time, the oil-based material produced by the oil-based material-producing microorganisms may be obtained by extracting a mixture of the oil-based material and solvent and then removing the solvent.

Note that the microwave irradiation step in the reactor 11 and the collecting step in the collecting tank 17 may be a process of a batch type or may be of a flow-through type.

Experimental Example

Next, a process that produces an oil-based material from microalgae using the oil-based material-producing apparatus 1 according to this example will be described with reference to an experimental example. It will be appreciated that the present invention is not limited to this experimental example.

In this experimental example, microalgae were irradiated with microwaves in the presence of the microwave responsive material. As the microwave responsive material, granular carbon was used. Furthermore, in this experimental example, agitation was performed by the agitation unit 23. As the agitation unit 23, a magnetic stirrer was used. As the microalgae, *Scenedesmus* (*Scenedesmus* sp.) was used. After concentration, *Scenedesmus* was diluted 10-fold by mass ratio with ultrapure water, and was then irradiated with microwaves. Furthermore, as comparative examples, *Scenedesmus* samples that had been diluted 10-fold by mass ratio in a similar manner were respectively irradiated with ultrasonic waves and placed in an oil bath.

In the microwave irradiation, the temperature of the microalgae was controlled at 80° C. Furthermore, also in the oil bath, the temperature was controlled at 80° C. The ultrasonic wave irradiation was performed at room temperature. Furthermore, the duration time for the microwave irradiation, the duration time for the ultrasonic wave irradiation, and the duration time for the oil bath were all 10 minutes each. Note that the duration time for the microwave irradiation and the duration time for the oil bath were both the time after the temperature was increased. In the microwave irradiation, the temperature was increased from room temperature to 80° C. at a rate of 10° C./min.

Subsequently, the amount of oil-based material was measured. The amount of oil-based material obtained with the microwave irradiation was about 1 ml per 10 g of *Scenedesmus*. A slight amount of oil-based material was obtained also with the oil bath, but the amount was as small as 0.5 ml or less per 10 g of *Scenedesmus*. Furthermore, no oil-based material was detected in the case of the ultrasonic wave irradiation.

This experimental example shows that an oil-based material produced by microalgae, which are oil-based material-producing microorganisms, can be efficiently collected by irradiating the microalgae with microwaves. The reason for this seems to be that microwave irradiation can directly heat moisture in the cells of microalgae and can break at least part of the cell membranes of the microalgae. In this experimental example, granular carbon was used as the microwave responsive material, but carbon composites may be used instead.

In this manner, the method and the apparatus 1 for producing an oil-based material according to this example can collect the oil-based material produced by the oil-based material-producing microorganisms by irradiating the oil-based material-producing microorganisms with microwaves. At that time, it is sufficient that only microwaves are irradiated, and, thus, the oil-based material can be efficiently produced using a simple method that, for example, does not require the temperature and the pressure to be kept high as in conventional examples. Furthermore, it seems that, since the oil-based material produced by the oil-based material-producing microorganisms is collected by the microwave irradiation, the energy required to collect the same amount of oil-based material is smaller than that in conventional examples.

Figure 4:
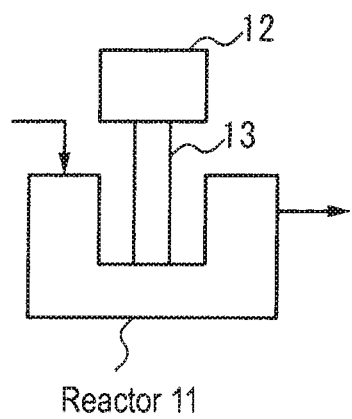
FIG. 4 is a view showing an exemplary shape of the reactor according to the example.

Note that, in this example, at least part of the reactor 11 may have a shape that allows microwaves generated by the microwave generator 12 to be concentrated and irradiated on that part. For example, as shown in FIG. 4, part of the reactor 11 may be formed shallow (thin) such that microwaves are irradiated on that position. In this manner, the oil-based material-producing microorganisms at that position can be effectively irradiated with microwaves. As described above, the depth to which microwaves penetrate is fixed, and, thus, if part of the reactor 11 is formed at a height (or width or length) substantially corresponding to the penetration depth, microwaves are concentrated and irradiated on the oil-based material-producing microorganisms at that position.

Furthermore, in this example, a mixing portion that mixes the oil-based material-producing microorganisms and the flowing microwave responsive material may be provided on the path before the reactor 11. In that case, the oil-based material-producing microorganisms and the microwave responsive material that have been mixed by the mixing portion are loaded into the reactor 11.

Furthermore, in this example, a case was described in which the microwave responsive material is able to flow, but there is no limitation to this. For example, the microwave responsive material may be immobilized. In that case, for example, the microwave responsive material may be directly immobilized on the reactor 11 or may be immobilized via another member on the reactor 11. The microwave responsive material may be immobilized, for example, by being pasted on the inner wall of the reactor 11 or by being filled in a filling layer, a column, or the like inside the reactor 11. Examples of the shape of the microwave responsive material include various grains, a cylinder (that may be or may not be hollow), a sphere, a pellet, a ring, a shell, a honeycomb, a foam, a fiber, a cloth, a plate, and other shapes. Note that, if at least part of the reactor 11 has a shape that allows microwaves generated by the microwave generator 12 to be concentrated and irradiated on that part, for example, the immobilized microwave responsive material may be arranged at that position on which microwaves are concentrated and irradiated.

Furthermore, in this example, a case was described mainly in which, in the microwave irradiation step, microwaves are irradiated in the presence of the microwave responsive material, but there is no limitation to this. For example, as in the above-described experimental example, in the microwave irradiation step, microwaves may be irradiated in the absence of the microwave responsive material. In that case, the microwave responsive material does not have to be loaded into the reactor 11, and does not have to be present in the reactor 11.

Furthermore, in this example, a process that crushes the oil-based material-producing microorganisms using a crushing unit may be performed in the microwave irradiation step, before the microwave irradiation step, after the microwave irradiation step, or at combined timings of any two or more thereof. There is no limitation on the crushing unit, as long as it can crush the oil-based material-producing microorganisms. Examples of the crushing unit include an ultrasonic wave homogenizer, a rotating blade homogenizer, a high pressure homogenizer, a bead-based homogenizer, and other crushing units. The oil-based material can be efficiently collected by causing the crushing unit to crush the oil-based material-producing microorganisms. Preferably, the crushing unit does not crush the microwave responsive material. Thus, for example, the crushing process may be performed on the oil-based material-producing microorganisms, before mixing the oil-based material-producing microorganisms and the microwave responsive material, after causing the microwave responsive material separating portion 15 to separate the microwave responsive material, or so as not to crush the microwave responsive material in a state where the oil-based material-producing microorganisms and the microwave responsive material have been mixed. In order to perform the crushing process so as not to crush the microwave responsive material, the oil-based material-producing microorganisms and the microwave responsive material may be separated, and the separated oil-based material-producing microorganisms may be subjected to the crushing process. For the separation, for example, a punching board or a net having a large number of holes through which the microwave responsive material cannot pass but the oil-based material-producing microorganisms can pass.

Figure 5A:
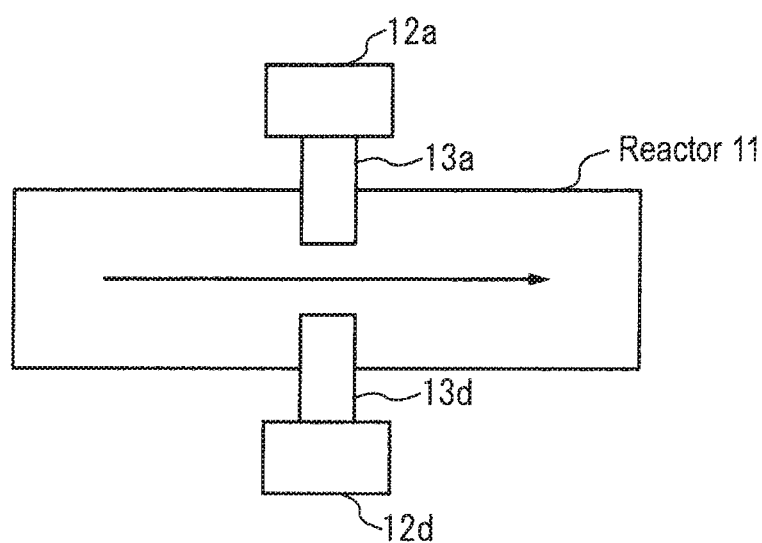
FIG. 5A is a view illustrating a position for microwave irradiation according to the example.
Figure 5B:
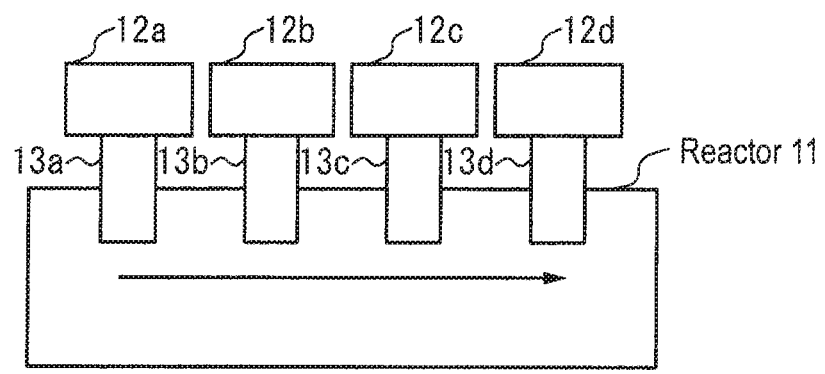
FIG. 5B is a view illustrating positions for microwave irradiation according to the example.

Furthermore, in the microwave irradiation step in this example, microwaves having two or more frequencies may be irradiated. In that case, microwaves having two or more frequencies may be irradiated on the same position, or may be respectively irradiated on different positions. For example, as shown in FIG. 5A, microwaves having frequencies X and Y respectively generated by microwave generators 12a and 12d may be irradiated on the same position in the reactor 11, that is, at the midstream in the reactor 11. Note that the microwaves having the frequencies X and Y are respectively transmitted via waveguides 13a and 13d to the reactor 11. Furthermore, for example, as shown in FIG. 5B, microwaves having a frequency X generated by microwave generators 12a, 12b, and 12c may be irradiated on the side from the upstream to the midstream in the reactor 11, and microwaves having a frequency Y generated by a microwave generator 12d may be irradiated on the downstream side in the reactor 11. Note that the microwaves having the frequency X are respectively transmitted via waveguides 13a, 13b, and 13c to the reactor 11. Furthermore, the microwaves having the frequency Y are transmitted via a waveguide 13d to the reactor 11. FIGS. 5A and 5B are both views of the reactor 11 from above, and the arrows in the drawings indicate the flow of reaction materials inside the reactor 11. If microwaves having two or more frequencies are irradiated, the number of frequencies may be two, or three or more. There is no limitation on the combination of two or more frequencies, as long as they are selected from the range from 300 MHz to 300 GHz. For example, if microwaves having two frequencies are irradiated, examples of the combination of these frequencies include 2.45 GHz and 5.8 GHz, 2.45 GHz and 24 GHz, 2.45 GHz and 913 MHz, 5.8 GHz and 24 GHz, 5.8 GHz and 913 MHz, and 24 GHz and 913 MHz. Furthermore, if microwaves having two or more frequencies are irradiated, there is no limitation on the irradiation timing. For example, microwaves having two or more frequencies may be simultaneously irradiated, or may be irradiated such that the frequencies respectively correspond to different irradiation periods. For example, in the latter case, microwaves having the frequency X may be irradiated in one period, and microwaves having the frequency Y may be irradiated in the next period. Note that if microwaves having two or more frequencies are irradiated, a material that is not affected by the action (e.g., heating, etc.) of microwaves having one frequency can be also affected, and, thus, a wider range of materials can be affected by the microwaves.

Furthermore, in the microwave irradiation step in this example, a mixture of the oil-based material-producing microorganisms and organic solvent may be irradiated with microwaves. Preferably, the organic solvent has a high affinity for the oil-based material that is to be collected.

Examples of the organic solvent include hexane and chloroform-methanol mixed liquid. Furthermore, a mixture of the oil-based material-producing microorganisms and organic solvent may be irradiated with microwaves, or a mixture of the oil-based material-producing microorganisms, organic solvent, and water may be irradiated with microwaves. If a mixture of the oil-based material-producing microorganisms and organic solvent is irradiated with microwaves, for example, the oil-based material-producing microorganisms that have been dried and the organic solvent may be mixed and placed in the reactor 11. Note that, in the microwave irradiation step of irradiating the mixture of the oil-based material-producing microorganisms and the organic solvent with microwaves, microwave may be irradiated in the presence of the microwave responsive material as described above. Furthermore, if the mixture of the oil-based material-producing microorganisms and the organic solvent is irradiated with microwaves in the microwave irradiation step, a unit that mixes the oil-based material-producing microorganisms and the organic solvent may be provided on the path before the reactor 11. Furthermore, if the organic solvent is used, a process that removes the organic solvent is preferably performed in the collecting step. Examples of the process include distillation.

Furthermore, in this example, a case was described in which the oil-based material-producing apparatus 1 is provided with the temperature measuring portion 24 and the microwave control portion 14, but there is no limitation to this. For example, if the temperature is not controlled or if the internal portion of the reactor 11 can be kept at a desired temperature or in a desired temperature range by setting the power of microwaves to a predetermined value, the power of microwaves does not have to be controlled using the temperature.

Furthermore, in this example, a case was described in which the microwave responsive material separating portion 15 is provided on the path after the reactor 11, but there is no limitation to this. If the oil-based material-producing apparatus 1 according to this example does not have to separate the microwave responsive material, for example, because of using another device to separate the microwave responsive material, using an immobilized microwave responsive material, or not using the microwave responsive material, the microwave responsive material separating portion 15 does not have to be provided.

Furthermore, in this example, a case was described in which the agitation unit 23 that agitates the content inside the reactor 11 is provided, but there is no limitation to this. For example, if the reactor 11 has a configuration that allows the entire content to be easily irradiated with microwaves (e.g., if the inner diameter of the reactor 11 is small, etc.), the agitation unit 23 does not have to be provided.

Furthermore, in this example, a case was described in which the oil-based material-producing apparatus 1 is provided with the collecting tank 17, but there is no limitation to this. For example, another device may be used to perform processes such as collecting of the oil-based material produced by the oil-based material-producing microorganisms.

Furthermore, in the foregoing example, each processing or each function may be realized by integrated processing by a single apparatus or a single system, or alternatively, may be realized by distributed processing by multiple apparatuses or multiple systems.

Furthermore, in the foregoing example, the oil-based material-producing method may be realized using the oil-based material-producing apparatus 1, or using other apparatuses. Furthermore, the oil-based material-producing method according to the foregoing example may be a method including at least part of the processing of a method for producing an oil-based material by collecting the oil-based material produced by the oil-based material-producing microorganisms. That is to say, for example, the oil-based material-producing method may include only the microwave irradiation step, or may include the microwave irradiation step and the collecting step.

Furthermore, in the foregoing example, information such as a threshold value, a numerical expression, or an address used in each constituent element in the processing and the like may be retained in a storage medium (not shown) temporarily or for a long period of time even if not specified in the description above. Furthermore, information may be accumulated in the storage medium (not shown) by each constituent element or an accumulating portion (not shown). Furthermore, information may be read from the storage medium (not shown) by each constituent element or a reading portion (not shown).

Furthermore, in the foregoing example, if information used in each constituent element or the like, for example, information such as a threshold value, an address, or various setting values used in each constituent element in the processing may be changed by a user, the user may change such information as appropriate even if not specified in the description above, but there is no limitation to this. If the user may change such information, the change may be realized by, for example, an accepting portion (not shown) that accepts a change instruction from the user and a changing portion (not shown) that changes information according to the change instruction. The change instruction may be accepted by the accepting portion (not shown), for example, by accepting information from an input device, by receiving information transmitted via a communication line, or by accepting information read from a predetermined storage medium.

Furthermore, in the foregoing example, each constituent element may be configured by dedicated hardware, or alternatively, constituent elements that can be realized as software may be realized by executing a program. For example, each constituent element may be realized by a program execution portion such as a CPU reading and executing a software program stored in a storage medium such as a hard disk or a semiconductor memory.

Furthermore, it will be appreciated that the present invention is not limited to the example set forth herein, and various modifications are possible within the scope of the present invention.

As described above, the method and the apparatus for producing an oil-based material according to the present invention are effective in that the oil-based material can be efficiently collected by irradiating oil-based material-producing microorganisms with microwaves, and, thus, they are useful, for example, as a method for producing an oil-based material using the oil-based material-producing microorganisms.

The invention claimed is:
1. An oil-based material-producing method, comprising:
 a placing step of adding water as a dispersion medium and oil-based material-producing microorganisms to a reactor to produce an aqueous slurry consisting of the water, the oil-based material-producing microorganisms and a microwave responsive material;
 a microwave irradiation step of irradiating the aqueous slurry in the reactor with microwaves, breaking at least part of the cell walls of the oil-based material-producing microorganisms; and collecting an oil-based material produced by the oil-based material-producing microorganisms after the microwave irradiation step,
wherein, in the microwave irradiation step, when the oil-based material-producing microorganisms are irradiated with microwaves in a presence of the microwave responsive material, the microwave responsive material is either one of a microwave-absorbing material and a microwave-sensitive material,
wherein the microwave responsive material is able to flow,
wherein the microwave responsive material has a shape for collecting electric field of microwaves,
wherein the microwave responsive material is a conductive substance, and
wherein the shape of the microwave responsive material is a grain shape having a surface provided with multiple pointed projections.

2. The oil-based material-producing method according to claim 1, wherein the oil-based material-producing microorganisms are oil-based material-producing microalgae.

3. The oil-based material-producing method according to claim 1, wherein the microwave responsive material consists of one or more of iron, nickel and cobalt, metal oxides, and non-fullerene carbon.

4. The oil-based material-producing method according to claim 1, wherein the microwave irradiation step further comprises the step of rapidly heating and evaporating moisture within the oil-based material-producing microorganisms.

5. An oil-based material-producing method, comprising:
a placing step of adding water as a dispersion medium and oil-based material-producing microorganisms to a reactor to produce an aqueous slurry consisting of the water and the oil-based material-producing microorganisms;
a microwave irradiation step of irradiating the aqueous slurry in the reactor with microwaves, breaking at least part of the cell walls of the oil-based material-producing microorganisms;
a collection step of collecting an oil-based material produced by the oil-based material-producing microorganisms after the microwave irradiation step; and
a discharging step of discharging the oil-based material-producing microorganisms from the reactor,
wherein, in the microwave irradiation step, the aqueous slurry is irradiated with microwaves having at least first and second frequencies,
wherein the oil-based material-producing microorganisms are placed in the reactor that is a flow-through type having an upstream side and a downstream side,
wherein the reactor has an unfilled space in an upper portion inside the reactor,
wherein microwaves having the first frequency are irradiated to the slurry through the unfilled space at the upstream side,
wherein microwaves having the second frequency are irradiated to the slurry through the unfilled space at the downstream side, and
wherein the microwave irradiation step and the discharging step are continuously and gradually performed.

6. The oil-based material-producing method according to claim 5, wherein the aqueous slurry further consists of a microwave responsive material that is a conductive sub stance.

7. The oil-based material-producing method according to claim 5, wherein the aqueous slurry in the reactor is agitated by an agitation unit to substantially uniformly irradiate the aqueous slurry with microwaves.

8. The oil-based material-producing method according to claim 5, wherein the reactor is partitioned into two or more chambers.

9. An oil-based material-producing method, comprising:
a placing step of adding water as a dispersion medium and oil-based material-producing microorganisms to a reactor to produce an aqueous slurry consisting of the water and the oil-based material-producing microorganisms;
a microwave irradiation step of irradiating the aqueous slurry, placed in the reactor with microwaves, breaking at least part of the cell walls of the oil-based material-producing microorganisms;
a collection step of collecting an oil-based material produced by the oil-based material-producing microorganisms after the microwave irradiation step; and
a discharging step of discharging the oil-based material-producing microorganisms from the reactor,
wherein the reactor has an unfilled space in an upper portion inside the reactor,
wherein the inner wall of the reactor is made of a material that reflects microwaves,
wherein the aqueous slurry is irradiated with microwaves through the unfilled space, and
wherein the microwave irradiation step and the discharging step are continuously and gradually performed.

10. The oil-based material-producing method according to claim 9, wherein the reactor is of a horizontal flow-through type.

11. The oil-based material-producing method according to claim 9, wherein, in the microwave irradiation step, the aqueous slurry is irradiated with microwaves in a presence of a microwave responsive material, which is either one of a microwave-absorbing material and a microwave-sensitive material.

12. The oil-based material-producing method according to claim 11, wherein the microwave responsive material is able to flow.

13. The oil-based material-producing method according to claim 11, wherein the microwave responsive material is a conductive substance.

14. The oil-based material-producing method according to claim 9, wherein the oil-based material-producing microorganisms are oil-based material-producing microalgae.

15. The oil-based material-producing method according to claim 9, wherein the aqueous slurry in the reactor is agitated by an agitation unit to substantially uniformly irradiate the aqueous slurry with microwaves.

16. The oil-based material-producing method according to claim 9, wherein the reactor is partitioned into two or more chambers.

17. The oil-based material-producing method according to claim 9, wherein the reactor is connected to a waveguide transmitting microwaves to the unfilled space in the upper portion inside the reactor.

18. The oil-based material-producing method according to claim 9,
wherein, in the collecting step, an oil layer, which is a layer of the oil-based material and is separated from a water layer, is collected.

* * * * *